United States Patent
Pan et al.

(10) Patent No.: US 11,807,601 B2
(45) Date of Patent: Nov. 7, 2023

(54) ELECTROLYTE AND COMPOUND FOR THE ELECTROLYTE AND CAPACITOR

(71) Applicant: INDUSTRIAL TECHNOLOGY RESEARCH INSTITUTE, Hsinchu (TW)

(72) Inventors: Che-Wei Pan, Hsinchu (TW); Chiu-Tung Wang, Tianwei Township (TW); Li-Duan Tsai, Hsinchu (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 490 days.

(21) Appl. No.: 17/131,356

(22) Filed: Dec. 22, 2020

(65) Prior Publication Data

US 2022/0127219 A1    Apr. 28, 2022

(30) Foreign Application Priority Data

Oct. 23, 2020  (TW) .................................. 109136848

(51) Int. Cl.
| | | |
|---|---|---|
| C07C 69/34 | (2006.01) | |
| H01G 9/035 | (2006.01) | |
| H01G 9/02 | (2006.01) | |
| H01G 9/045 | (2006.01) | |

(52) U.S. Cl.
CPC .............. *C07C 69/34* (2013.01); *H01G 9/02* (2013.01); *H01G 9/035* (2013.01); *H01G 9/045* (2013.01)

(58) Field of Classification Search
CPC ......... C07C 69/34; H01G 9/035; H01G 9/045
See application file for complete search history.

(56) References Cited

U.S. PATENT DOCUMENTS

| | | | | |
|---|---|---|---|---|
| 6,307,732 | B1 * | 10/2001 | Tsubaki .................. | H01G 9/022 252/62.2 |
| 7,485,240 | B1 * | 2/2009 | Feger ...................... | H01G 9/035 252/62.2 |
| 8,279,581 | B2 | 10/2012 | Takaok | |
| 2007/0194286 | A1 | 8/2007 | Chiba | |
| 2016/0148756 | A1 * | 5/2016 | Wada ...................... | H01G 11/62 252/62.2 |

FOREIGN PATENT DOCUMENTS

| | | | |
|---|---|---|---|
| CN | 101887803 | * | 10/2010 |
| CN | 101887803 A | | 11/2010 |
| CN | 1607618 A | | 3/2013 |
| CN | 102969161 A | | 3/2013 |
| CN | 1040222308 A | | 9/2014 |
| CN | 105152942 A | | 12/2015 |
| CN | 105990027 A | | 10/2016 |
| CN | 109935468 A | | 6/2019 |
| CN | 110249468 A | | 9/2019 |
| CN | 111524709 A | | 8/2020 |
| JP | 60-136216 A | | 7/1985 |
| JP | 02-062026 | * | 3/1990 |
| JP | 2000-188240 A | | 7/2000 |
| JP | 2001-068382 | * | 2/2001 |
| JP | 2005-45089 A | | 2/2005 |
| JP | 2005-166889 A | | 6/2005 |
| JP | 3799442 | * | 7/2006 |
| JP | 2007-273921 A | | 10/2007 |
| JP | 2010-232630 A | | 10/2010 |
| JP | 2015-118841 A | | 6/2015 |
| JP | 60-226117 A | | 7/2015 |
| JP | 2017-55060 A | | 3/2017 |
| JP | 2017-85092 A | | 5/2017 |

(Continued)

OTHER PUBLICATIONS

Translation for JP 02-062026, Mar. 1, 1990.*
Taiwanese Office Action and Search Report for Taiwanese Application No. 109136848, dated Nov. 12, 2021.
Japanese Office Action for Japanese Application No. 2021-125649, dated Aug. 16, 2022, with English translation.
Chinese Office Action and Search Report for Chinese Application No. 202011460373.9 dated Jun. 14, 2023.

*Primary Examiner* — C Melissa Koslow
(74) *Attorney, Agent, or Firm* — Birch, Stewart, Kolasch & Birch, LLP

(57) ABSTRACT

An electrolyte is provided, which includes organic solvent; and (1) a compound and an ammonium salt thereof, (2) a diacid and an ammonium salt thereof, or (3) a combination thereof. The compound has a chemical structure of

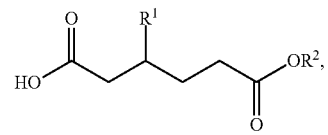

wherein $R^1$ is $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8. The diacid has a chemical structure of

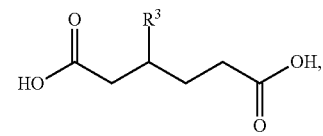

wherein $R^3$ is $C_{1-8}$ alkyl group, $C_{1-8}$ alkenyl group, $C_{1-8}$ alkynyl group, or aromatic group.

16 Claims, No Drawings

(56) References Cited

FOREIGN PATENT DOCUMENTS

| JP | 2019-29598 A | 2/2019 |
| JP | 2019-102791 A | 6/2019 |
| JP | 2019-179852 A | 10/2019 |
| TW | 201526343 A | 7/2015 |
| TW | I602205 B | 10/2017 |
| TW | 202008404 A | 2/2020 |
| WO | WO 2016-176938 A1 | 11/2016 |
| WO | WO 2017/170169 * | 10/2017 |

* cited by examiner

ELECTROLYTE AND COMPOUND FOR THE ELECTROLYTE AND CAPACITOR

CROSS-REFERENCE TO RELATED APPLICATIONS

This application claims the priority benefit of Taiwan application serial no. 109136848, filed on Oct. 23, 2020. The entirety of the above-mentioned patent application is hereby incorporated by reference herein.

TECHNICAL FIELD

The disclosure relates to a capacitor, and more particularly to a compound used in the composition of an electrolyte of the capacitor.

BACKGROUND

Aluminum electrolytic capacitors are energy storage devices that are regularly used as power supply filter capacitors. The main structure of an aluminum electrolytic capacitor comprises a capacitor element, an electrolyte, a case, and a rubber seal. The capacitor element is constructed by winding an anode aluminum foil and a cathode aluminum foil with a separator interposed therebetween. After impregnating the capacitor element in the electrolyte, the capacitor element is built into the case, and sealed with the rubber seal.

In order to maintain the high withstand voltage characteristics of the aluminum electrolytic capacitor, diacids and ammonium salts thereof are often dissolved in organic solvents to prepare the electrolyte. However, as the demand for higher operable ranges in working voltage and operating temperature of aluminum electrolytic capacitor (applicable in vehicle power supplies and household appliances) increases; standard electrolytes have gradually been unable to meet the requirements for those aluminum electrolytic capacitors of medium and high voltage, such as high withstand voltage, high electrical conductivity, and high spark voltage, thus limiting the market application of the aluminum electrolytic capacitors. Therefore, a new electrolyte composition is needed, to resolve the above-mentioned issues.

SUMMARY

According to an embodiment of the disclosure, a compound used in an electrolyte, having a chemical structure of:

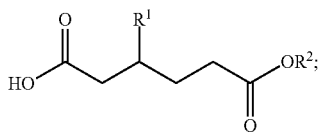

wherein $R^1$ is a $C_{1-8}$ is alkyl group, $C_{1-8}$ alkenyl group, $C_{1-8}$ alkynyl group, or aromatic group; and $R^2$ is —$(C_nH_{2n})$—OH, and n is an integer from 2 to 8.

According to an embodiment of the disclosure, an electrolyte comprises: an organic solvent; and (1) a compound and an ammonium salt thereof, (2) a diacid and an ammonium salt thereof, or (3) a combination of (1) and (2), wherein the compound has a chemical structure of:

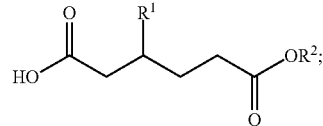

wherein $R^1$ is a $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8; wherein the diacid has a chemical structure of:

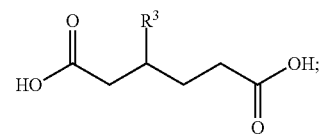

wherein $R^3$ is $C_{1-8}$ alkyl group, $C_{1-8}$ alkenyl group, $C_{1-8}$ alkynyl group, or aromatic group.

According to an embodiment of the disclosure, a capacitor comprises a capacitor element and the above-mentioned electrolyte, wherein the capacitor element comprises an anode aluminum foil; a cathode aluminum foil; and a separator, interposed therebetween the anode aluminum foil and the cathode aluminum foil; wherein the capacitor element is impregnated with the electrolyte.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to an embodiment of the disclosure, a compound used in an electrolyte, having a chemical structure of:

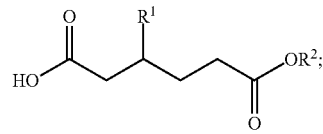

wherein $R^1$ is a $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8. In some embodiments, $R^1$ is methyl or tert-butyl, and n is 2. It is worth noting that if $R^1$ is H, or $R^1$ is substituted in other positions, for example

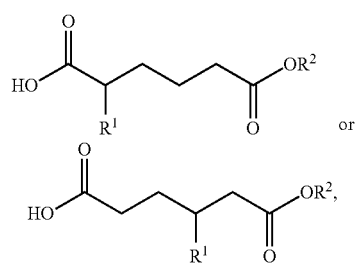

or then the compound is not suitable for the electrolyte. On the other hand, if n is too small (such as 1) or too large (such as 9), then the compound is not suitable for the electrolyte.

According to an embodiment of the disclosure, an electrolyte comprises organic solvent; and (1) a compound and an ammonium salt thereof, (2) a diacid and an ammonium salt thereof, or (3) a combination of (1) and (2). The compound has chemical structure of:

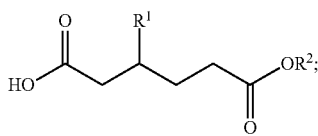

wherein $R^1$ is a $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8. If $R^1$ is substituted in other positions, then the compound and the ammonium salt thereof are not suitable for the electrolytes. If n is too small or too large, then the compound is not suitable for the electrolytes. The diacid has a chemical structure of:

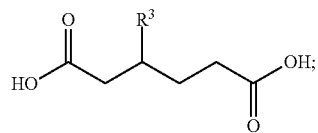

wherein $R^3$ is a $C_{1-8}$ alkyl group, $C_{1-8}$ alkenyl group, $C_{1-8}$ alkynyl group, or aromatic group. If $R^3$ is H, or $R^3$ is substituted in other positions (such as

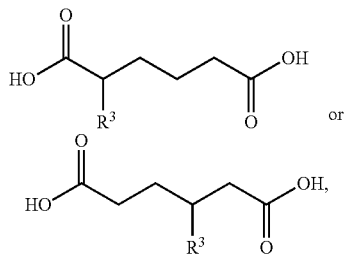

then the diacid and the ammonium salt thereof are not suitable for the electrolytes.

In some embodiments, a method for forming (1) the compound and the ammonium salt thereof is described as follows. Add the compound to an appropriate amount of aqueous ammonia, such as primary amine, secondary amine, tertiary amine, or a combination thereof; in the subsequent neutralization, part (not all) of the compound forms an ammonium salt. The pH of the neutralized mixture is about 6 to 7 (weakly acidic). Thereafter, filter the mixture solution to obtain filter cake containing a mixture of the compound and the ammonium salt thereof.

In some embodiments, a method for forming (2) the diacid and the ammonium salt thereof is described as follows. Add the diacid to an appropriate amount of aqueous ammonia, such as primary amine, secondary amine, tertiary amine, or a combination thereof; in the subsequent neutralization, part (not all) of the diacid forms an ammonium salt. The pH of the neutralized mixture is about 6 to 7 (weakly acidic). Thereafter, filter the mixture solution to obtain filter cake containing a mixture of the diacid and the ammonium salt thereof.

In some embodiments, (3) the combination thereof (suchas the combination of (1) the compound and the ammonium salt thereof, and (2) the diacid and the ammonium salt thereof) are formed as follows. Add the compound and the diacid to an appropriate amount of aqueous ammonia, such as primary amine, secondary amine, tertiary amine, or a combination thereof; in the subsequent neutralization, part (not all) of the compound and diacid form an ammonium salt. The pH of the neutralized mixture is about 6 to 7 ((weakly acidic). Thereafter, filter the mixture solution to obtain filter cake containing a mixture of (1) the compound and the ammonium salt thereof, and (2) the diacid and the ammonium salt thereof.

In some embodiments, the electrolyte comprises only (1) the compound and the ammonium salt thereof. In some embodiments, the electrolyte comprises only (2) the diacid and the ammonium salt thereof. In some embodiments, the electrolyte may comprise (3) the combination thereof, which is, a combination of (1) the compound and the ammonium salt thereof, and (2) the diacid and the ammonium salt thereof. For example, in (3) the combination thereof, (1) the compound and the ammonium salt thereof and (2) the diacid and the ammonium salt thereof have a weight ratio of 0.01:1 to 1.5:1, or 0.02:1 to 0.45:1. The weight ratio in the combination thereof can further improve the performance of the electrolyte such as conductivity at 30° C. and spark voltage at 85° C., as well as the performance of the capacitor such as capacitance, dissipation factor (DF), equivalent series resistance (ESR), and leakage current.

In some embodiments, the electrolyte may further comprise polyethylene glycol, polyvinyl alcohol, polyacryl alcohol, polyethylene oxide, propylene oxide ether, polymerized fatty acid, silicon dioxide, polyglyceride, dichromium ammonium acid, citric acid, or a combination of the above, so as to improve the performance of electrolyte and capacitor. For example, silica such as colloidal silica can be added, and the particle size of the silica can be 10 nm to 200 nm, such as 10 nm to 100 nm. In some embodiments, the weight of (1) the compound and the ammonium salt thereof, (2) the diacid and the ammonium salt thereof, or (3) the combination thereof, to the weight of polyethylene glycol, polyvinyl alcohol, polyacryl alcohol, polyethylene oxide, propylene oxide ether, polymeric fatty acid, silicon dioxide, polyglyceride, ammonium dichromate, citric acid, or a combination have a ratio of 1:0.01 to 1:0.5.

In some embodiments, the organic solvent comprises ethylene glycol, diethylene glycol, propylene glycol, 1,4-butanediol, glycerol, N,N-dimethylformamide, gamma-butyrolactone, propylene carbonate, ethylene carbonate, diethyl carbonate, diethylene glycol methyl ether, diethylene glycol monobutyl ether, gamma-valerolactone, or a combination thereof. For example, the weight of (1) the compound and the ammonium salt thereof, (2) the diacid and the ammonium salt thereof, or (3) the combination thereof to the weight of the organic solvent have a ratio of 1:6 to 1:10. If the amount of the organic solvent is too low, the electrolyte will become viscous, affecting the impregnability of the capacitor element. If the amount of the organic solvent is too high, the conductivity of the electrolyte will be low, which is deleterious to the performance of the capacitor.

According to an embodiment of the disclosure, a capacitor comprises a capacitor element and the above-mentioned electrolyte, wherein the capacitor element comprises an anode aluminum foil; a cathode aluminum foil; and a separator, interposed therebetween the anode aluminum foil and the cathode aluminum foil; wherein the capacitor element is impregnated with the electrolyte. Please refer to WO 2017/170169 A1 for description about the capacitor and the capacitor element, which is not detailed here.

Several examples with the accompanying drawing are described in detail below, to make the aforementioned features and advantages of the present disclosure comprehensible.

Preparation Example 1

30.21 g (0.438 mole) of sodium nitrate, 63 g (3.5 mole) of deionized water and 350 mL of nitric acid were mixed thoroughly, while maintaining the reaction temperature at 70° C. After reacting for 30 minutes, 27.37 g (0.175 mole) of 4-tert-butylcyclohexanol was dropwise added into the above mixture, while maintaining the reaction temperature at 70° C. for five hours. The mixture solution was then concentrated under reduced pressure and further extracted and purified to obtain compound 1a (26.8 g), which hydrogen spectrum was as follows: $^1$H NMR (CDCl$_3$-d1, 500 MHz): δ 2.52. (1H, dd, =16.32 Hz, 4.1 Hz), 2.48-2.35 (2H, m), 2.10 (1H, dd J=7.71 Hz, 16.27 Hz), 1.96-1.91 (1H, m), 1.75-1.70 (1H, m), 1.45-1.38 (1H, m), 0.91 (9H, s). The above reaction was as follows:

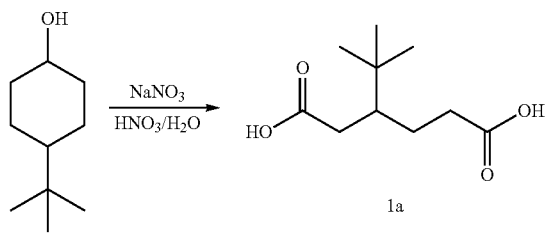

The product 1a (30 g) was dissolved in ethylene glycol (120 g) and reacted for 9 days to obtain a mixture of compound 1a and compound 1c (mole ratio=1:1), and the hydrogen spectra of the mixtures 1a and 1c were as follows: $^1$H NMR (D$_2$O-d2, 500 MHz): δ4.04 (1H, br), 3.64 (1H, br), 2.41-2.00 (4H, m), 1.79 (1H, br), 1.47 (1H, br), 1.22 (1H, br), 0.74 (9H, br). The above reaction was as follows:

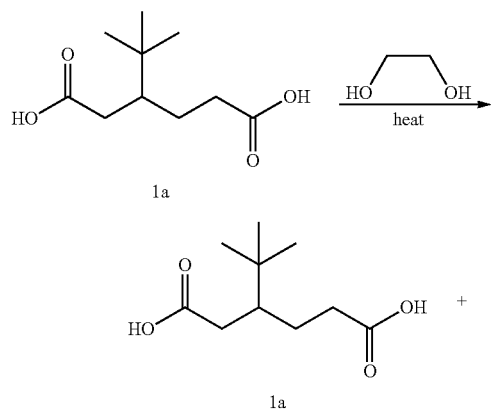

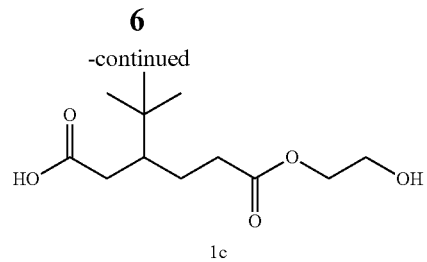

Preparation Example 2

30.2.1 g (0.438 mole) of sodium nitrate, 63 g (3.5 mole) of deionized water and 350 mL of nitric acid was mixed thoroughly, while maintaining the reaction temperature at 70° C. After reacting for 30 minutes, 20 g (0.175 mole) of 4-methylcyclohexanol was added dropwise into the above mixture, while maintaining the reaction temperature at 70° C. for five hours. The mixture solution was then concentrated under reduced pressure and further extracted and purified to obtain compound 1b (21 g), which hydrogen spectrum was as follows: $^1$H NMR (CDCl$_3$-1, 500 MHz): δ 2.45-2.18 (4H, m), 2.04-1.6 (1H, m), 1.57-1.96 (1H, m), 1.57-1.50 (1H, m), 0.98 (3H, d, J=6.68 Hz). The above reaction was as follows:

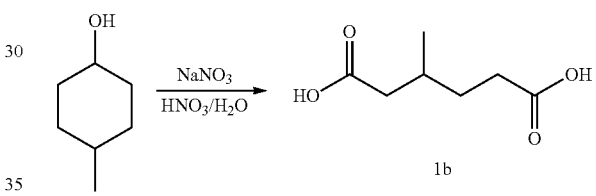

The product 1b (30 g) is dissolved in ethylene glycol (120 g) and reacted for 5 days to obtain a mixture of compound 1d, and its hydrogen spectra was as follows: $^1$H NMR (D$_2$O-d2, 500 MHz): δ4.04 (2H, br), 3.64 (2H, br), 2.34-2.05 (4H, m), 1.78 (1H, br), 1.52 (1H, br), 1.39 (1H, br), 0.80 (3H, br). The above reaction was as follows:

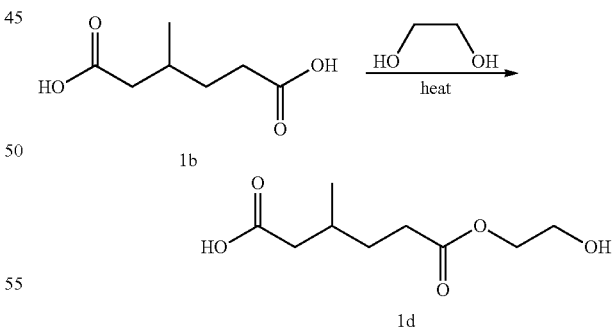

In the following embodiments, please refer to WO 2017/170169A1 for the measurement method of the conductivity at 30° C. and the spark voltage at 85° C. of the electrolyte.

In the following examples, the capacitor was constructed by the following steps: first, the area of an aluminum foil was expanded through etching (roughening) treatment, next an anode foil with oxide film layer was fabricated by chemical conversion treatment. In the same manner, the area of another aluminum foil was expanded through etching treatment to form a cathode foil. The foils are wound with separator interposed therebetween to form capacitor elements, wherein the anode foil and the cathode foil were connected with wire lead-out part. The capacitor element was then impregnated with electrolytes prepared by the following examples, and was mounted in a cylindrical aluminum case, whose bottom opening end was sealed with rubber resin, to obtain radial lead type electrolytic capacitor with a rated voltage of 450V, a rated capacitance of 2.2 µF, and the size of the capacitor was 8 mm in diameter and 11.5 mm in length. The electrical characteristic of the electrolytic capacitor were measured with methods described in CN 110199367A, which discloses the measurement methods of capacitor capacitance, loss factor (DF), equivalent series resistance and leakage current.

Below, exemplary embodiments will be described in detail with reference to accompanying drawings so as to be easily realized by a person having ordinary knowledge in the art. The inventive concept may be embodied in various forms without being limited to the exemplary embodiments set forth herein. Descriptions of well-known parts are omitted for clarity, and like reference numerals refer to like elements throughout.

Example 1

1.8 parts by weight of the compound 1c synthesized in Preparation Example 1 and 8.2 parts by weight of the diacid were added to an appropriate amount of aqueous ammonia to neutralize the solution, to convert partial amount of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt to the diacid and the ammonium salt of 0.22:1 The chemical structure of the above diacid was as follows:

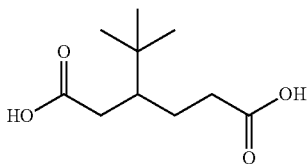

The aforementioned mixture and 2.5 parts by weight of colloidal silica (with a particle size of about 100 nm, purchased from Alfa Aesar, Silicon (IV) oxide, 0.1 micron particles in liquid) were added to 87.5 parts by weight of ethylene glycol, to form an electrolyte solution with a conductivity of 2.04 mS/cm at 30° C. and a spark voltage of 456V at 85° C. Radial lead type electrolytic capacitor constructed with the above prepared electrolyte, provided a capacitance of 2.33 µF, a loss factor (DF) of 3.82%, an equivalent series resistance (ESR) of 9043 mΩ, and a leakage current of 5.6 In addition, the product yield of the capacitor was 100%.

Example 2

A mixture of Example 1 and 5 parts by weight of colloidal silica with a particle size of about 100 nm were added to 85 parts by weight of ethylene glycol, to form an electrolyte solution with conductivity of 2.12 mS/cm at 30° C. and a spark voltage of 470V at 85° C. Radial lead type electrolytic capacitor constructed with the above prepared electrolyte, provided a capacitance of 2.33 µF, a loss factor (DF) of 3.78%, an equivalent series resistance (ESR) of 8620 mΩ, and a leakage current of 8.1 µA. In addition, the product yield of the capacitor was 100%. After exposing the electrolytic capacitor to a temperature of 125° C. for 1000 hours for reliability test, the capacitance value was 2.34 µF, the loss factor (DF) was 4.94%, the equivalent series resistance change (ΔESR) was 53%, and leakage current was 0.38 µA. The definition of ΔESR was as follows:

$$\Delta ESR(\%) = (ESR_{@125°\,C.,1000hr} - ESR_{initial})/ESR_{initial}$$

Example 3

A mixture of Example 1 and 5 parts by weight of colloidal silica (with a particle size of about 10 nm, purchased from Nissan Chemical ORGANOSILICASOL) were added to 85 parts by weight of ethylene glycol, to form an electrolyte solution with conductivity of 2.05 mS/cm at 30° C. and a spark voltage of 474V at 85° C. Radial lead type electrolytic capacitor constructed with the above prepared electrolyte, provided a capacitance of 2.33 µF, a loss factor (DF) of 3.63%, an equivalent series resistance (ESR) of 8678 mΩ, and a leakage current of 3.8 µA. In addition, the product yield of the capacitor was 100%. After exposing the electrolytic capacitor to a temperature of 125° C. for 1000 hours for reliability test, the capacitance value was 2.34 µF, the loss factor (DF) was 4990%, the equivalent series resistance change (ΔESR) was 50%, and leakage current was 0.56 µA.

Example 4

10 parts by weight of diacid was added to an appropriate amount of aqueous ammonia to neutralize the solution, to convert partial amount (not all) of the diacid to ammonium salt. The pH of the neutralized mixture was about 6 to 7 (weakly acidic). Thereafter, the mixture solution was filtered to obtain filter cake containing a mixture of the diacid and the ammonium salt thereof. The chemical structure of the above diacid was as follows:

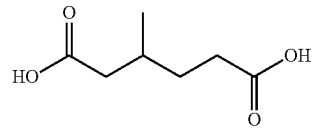

The aforementioned mixture and 5 parts by weight of colloidal silica with a particle size of about 100 nm were added to 85 parts by weight of ethylene glycol, to form an electrolyte solution with a conductivity of 2.12 mS/cm at 30° C. and a spark voltage of 453V at 85° C.

Example 5

10 parts by weight of the compound 1d of Preparation Example 2 was added to an appropriate amount of aqueous ammonia to neutralize the solution, to convert partial amount (not all) of the compound 1d to an ammonium salt. The pH of the neutralized mixture was about 6 to 7 (weakly acidic). Thereafter, the mixture solution was filtered to obtain filter cake containing a mixture of the compound 1d and the ammonium salt thereof.

The aforementioned mixture and 5 parts by weight of colloidal silica (with a particle size of about 100 nm) were added to 85 parts by weight of ethylene glycol, to form an electrolyte solution with a conductivity of 2.01 mS/cm at 30° C. and a spark voltage of 474V at 85° C.

Example 6

1.35 parts by weight of the compound 1c synthesized in Preparation Example 1 and 6.15 parts by weight of the diacid disclosed in Example 1 were added to an appropriate amount of aqueous ammonia to neutralize the solution, to convert partial amount (not all) of compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.22:1.

The aforementioned mixture and 5 parts by weight of colloidal silica (with a particle size of about 100 nm,) were added to 87.5 parts by weight of ethylene glycol, to form an electrolyte solution with a conductivity of 1.93 mS/cm at 30° C. and a spark voltage of 468V at 85° C. Radial lead type electrolytic capacitor constructed with the above prepared electrolyte, provided a capacitance of 2.32 µF, a loss factor (DF) of 3.84%, an equivalent series resistance (ESR) of 9602 mΩ, and a leakage current of 14.1 µA.

Example 7

2.25 parts by weight of the compound 1c synthesized in Preparation Example 1 and 10.25 parts by weight of thediacid disclosed in Example 1 were added to an appropriate amount of aqueous ammonia to neutralize the solution, to convert partial amount (not all) of the compound is and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.22:1.

The aforementioned mixture and 5 parts by weight of colloidal silica (with a particle size of about 100 nm,) were added to 82.5 parts by weight of ethylene glycol, to form an electrolyte solution with a conductivity of 2.34 mS/cm at 30° C. and a spark voltage of 459V at 85° C. Radial lead type electrolytic capacitor constructed with the above prepared electrolyte, provided a capacitance of 2.33 µF, a loss factor (DF) of 3.75%, an equivalent series resistance (ESR) of 8563 mΩ, and a leakage current of 7.5 µA.

Example 8

2.7 parts by weight of the compound 1c synthesized in Preparation Example 1 and 12.3 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound is and the ammonium salt thereof, and the diacid and the ammonium salt thereof, with a weight ratio of compound 1c and the ammonium salt thereof to the diacid and the ammonium salt thereof of 0.22:1.

The aforementioned mixture and 5 parts by weight of colloidal silica (with a particle size of about 100 nm,) were added to 80 parts by weight of ethylene glycol, to form an electrolyte solution with a conductivity of 2.45 mS/cm at 30° C. and a spark voltage of 458V at 85° C. Radial lead type electrolytic capacitor constructed with the above prepared electrolyte, provided a capacitance of 2.33 µF, a loss factor (DF) of 3.62%, am equivalent series resistance (ESR) of 8963 mΩ, and a leakage current of 5.9 µA.

Example 9

0.2 parts by weight of the compound 1c synthesized in Preparation Example 1 and 9.8 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.02:1.

The aforementioned mixture and 5 parts by weight of colloidal silica (with a particle size of about 100 nm,) were added to 85 parts by weight of ethylene glycol, to form an electrolyte solution with a conductivity of 2.10 mS/cm at 30° C. and a spark voltage of 466V at 85° C. Radial lead type electrolytic capacitor constructed with the above prepared electrolyte, provided a capacitance of 2.33 µf, a loss factor (DF) of 3.80%, an equivalent series resistance (ESR) of 8932 mΩ, and a leakage current of 12.2 µA.

Example 10

0.5 parts by weight of the compound is synthesized in Preparation Example 1 and 9.5 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.05:1.

The aforementioned mixture and 5 parts by weight of colloidal silica (with a particle size of about 100 nm,) added to 85 parts by weight of ethylene glycol, to form an electrolyte solution with a conductivity of 2.10 mS/cm at 30° C. and a spark voltage of 466V at 85° C. Radial lead type electrolytic capacitor constructed with the above prepared electrolyte, provided a capacitance of 2.33 µF, a loss factor (DF) of 3.63%, an equivalent series resistance (ESR) of 8151 mΩ, and a leakage current of 11.1 µA. After exposing the electrolytic capacitor to a temperature of 125° C. for 1000 hours for reliability test, the capacitance value was 2.34 µF, the loss factor (DF) was 4.84%, the equivalent series resistance change (ΔESR) was 55%, and leakage current was 0.40 µA.

Example 11

3 parts by weight of the compound 1c synthesized in Preparation Example 1 and 7 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.43:1.

The aforementioned mixture and 5 parts by weight of colloidal silica (with a particle size of about 100 nm) were added to 85 parts by weight of ethylene glycol, to form an electrolyte solution with a conductivity of 2.03 mS/cm at 30° C. and a spare voltage of 465V at 85° C. Radial lead type electrolytic capacitor constructed with the above prepared electrolyte, provided a capacitance of 2.33 µF, a loss factor (DF) of 4.02%, an equivalent series resistance (ESR) of 9528 and a leakage current of 11.7 µA. After exposing the electrolytic capacitor to a temperature of 125° C. for 1000 hours for reliability test, the capacitance value was 2.34 µF, the loss factor (DF) was 5.33%, the equivalent series resistance change (ΔESR) was 55%, and leakage current was 0.63 µA.

Example 12

3.8 parts by weight of the compound 1c synthesized in Preparation Example 1 and 6.2 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.61:1.

The aforementioned mixture and 5 parts by weight of colloidal silica (with a particle size of about 100 nm,) were added to 85 parts by weight of ethylene glycol, to form an electrolyte solution with a conductivity of 1.76 mS/cm at 30° C. and a spark voltage of 464 V at 85° C. Radial lead type electrolytic capacitor constructed with the above prepared electrolyte, provided a capacitance of 2.32 µF, a loss factor (DF) of 4.69%, an equivalent series resistance (ESR) of 10887 mΩ, and a leakage current of 11.7 µA. After exposing the electrolytic capacitor to a temperature of 125° C. for 1000 hours for reliability test, the capacitance value was 2.31 µf, the loss factor (DF) was 6.27%, the equivalent series resistance change (ΔESR) was 61%, and leakage current was 0.62 µA.

Example 13

4.5 parts by weight of the compound 1c synthesized in Preparation Example 1 and 5.5 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.82:1.

The aforementioned mixture and 5 parts by weight of colloidal silica (with a particle size of about 100 nm,) were added to 85 parts by weight of ethylene glycol, to form an electrolyte solution with a conductivity of 1.64 mS/cm at 30° C. and a spark voltage of 468 V at 85° C. Radial lead type electrolytic capacitor constructed with the above prepared electrolyte, provided a capacitance of 2.31 µF, a loss factor (DE) of 5.16%, an equivalent series resistance (ESR of 12308 mΩ, and a leakage current of 4.7 µA. After exposing the electrolytic capacitor to a temperature of 125° C. for 1000 hours for reliability test, the capacitance value was 2.3 µF, the loss factor (DF) was 6.52%, the equivalent series resistance change (ΔESR) was 61%, and leakage current was 0.46 µA.

Example 14

6 parts by weight of the compound 1c synthesized in Preparation Example 1 and 4 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 1.5:1.

The aforementioned mixture and 5 parts by weight of colloidal silica (with a particle size of about 100 nm,) were added to 85 parts by weight of ethylene glycol, to form an electrolyte solution with a conductivity of 1.56 mS/cm at 30° C. and a spark voltage of 473 V at 85° C. Radial lead type electrolytic capacitor constructed with the above prepared electrolyte, provided a capacitance of 2.30 µF, a loss factor (DF) of 6.02 an equivalent series resistance (ESR) of 16177 mΩ, and a leakage current of 3.9 µA.

Example 15

10 parts by weight of the diacid disclosed in Example 1 was added to an appropriate amount of aqueous ammonia to neutralize the solution, to convert partial amount (not all) of the diacid to ammonium salt. The pH of the neutralized mixture was about 6 to 7 (weakly acidic). Thereafter, the mixture solution was filtered to obtain filter cake containing the diacid and the ammonium salt thereof.

The aforementioned mixture and 5 parts by weight of colloidal silica with a particle size of about 100 nm,) were added to 85 parts by weight of ethylene glycol, to form an electrolyte solution with a conductivity of 2.08 mS/cm at 30° C. and a spark voltage of 464 V at 85° C. Radial lead type electrolytic capacitor constructed with the above prepared electrolyte, provided a capacitance of 2.32 µF, a loss factor (DF) of 4.27%, an equivalent series resistance (ESR) of 9303 mΩ, and a leakage current of 8.1 µA. After exposing the electrolytic capacitor to a temperature of 125° C. for 1000 hours for reliability test, the capacitance value was 2.33 µF, the loss factor (DF) as 5.59%, the equivalent series resistance change (ΔESR) was 67%, and leakage current was 1.80 µA.

Example 16

1.8 parts by weight of the compound 1c synthesized in Preparation Example 1 and 8.2 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.22:1.

The aforementioned mixture was added to 90 parts by weight of ethylene glycol, to form an electrolyte solution with a conductivity of 1.73 mS/cm at 30° C. and a spark voltage of 393 V at 85° C.

Example 17

1.8 parts by weight of the compound 1c synthesized in Preparation Example 1 and 8.2 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture was about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.22:1.

The aforementioned mixture and 1.5 parts by weight of colloidal silica (with a particle size of about 1.00 nm,) were added to 88.5 parts by weight of ethylene glycol, to form an electrolyte solution with a conductivity of 1.78 mS/cm at 30° C. and a spark voltage of 446 V at 85° C.

Example 18

1.8 parts by weight of the compound 1c synthesized in Preparation Example 1 and 8.2 parts by weight of the diacid disclosed in Example 1 were added to an appropriate amount of aqueous ammonia to neutralize the solution, to convert partial amount (not all) of the compound 1c and the diacid to ammonium salt. The pH of the neutralized mixture is about 6 to 7 (weakly acidic). Thereafter, the mixture solution was filtered to obtain filter cake containing a mixture of the compound 1c and the ammonium salt thereof, and the diacid and the ammonium salt thereof, with a weight ratio of the compound 1c and the ammonium salt thereof to the diacid and the ammonium salt thereof of 0.22:1.

The aforementioned mixture and 5 parts by weight of colloidal silica (with a particle size of about 200 nm, purchased from Alfa Aesar, Silicon (IV) oxide, 0.2 micron particles in liquid) were added to 85 parts by weight of ethylene glycol, to form an electrolyte solution with a conductivity of 2.08 mS/cm at 30° C. and a spark voltage of 462 V at 85° C. Radial lead type electrolytic capacitor constructed with the above prepared electrolyte, provided a capacitance of 2.32 μF, a loss factor (DF) of 3.92%, an equivalent series resistance (ESR) of 10032 mΩ, and a leakage current of 4.7 μA. The product yield of the capacitor was 80%.

Comparative Example 1

10 parts by weight of the diacid was added to an appropriate amount of aqueous ammonia to neutralize the solution, to convert partial amount (not all) of the diacid to ammonium salt. The pH of the neutralized mixture was about 6 to 7 (weakly acidic). Thereafter, the mixture solution was filtered to obtain filter cake containing a mixture of the diacid and the ammonium salt thereof. The chemical structure of the diacid in the present embodiment was as follows:

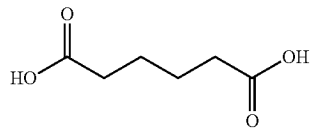

The aforementioned mixture and 5 parts by weight of colloidal silica (with a particle size of about 100 nm,) were added to 85 parts by weight of ethylene glycol, to form an electrolyte solution with a conductivity of 3.48 mS/cm at 30° C. and a spark voltage of 177 V at 85° C. The radial lead type electrolytic capacitor constructed with the electrolyte had insufficient withstand voltage.

Comparative Example 2

10 parts by weight of the diacid was added to an appropriate amount of aqueous ammonia to neutralize the solution, to convert partial amount (not all) of the diacid to ammonium salt. The pH of the neutralized mixture was about 6 to 7 (weakly acidic). Thereafter, the mixture solution was filtered to obtain filter cake containing a mixture of the diacid and the ammonium salt thereof. The chemical structure of the diacid in the present embodiment was as follows:

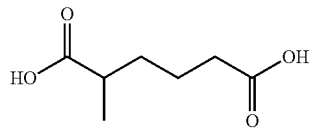

The aforementioned mixture and 5 parts by weight of colloidal silica (with a particle size of about 100 nm,) were added to 85 parts by weight of ethylene glycol, to form an electrolyte solution with a conductivity of 2.08 mS/cm at 30° C. and a spark voltage of 241 V at 85° C. The radial lead type electrolytic capacitor constructed with the electrolyte had insufficient withstand voltage.

Comparative Example 3

10 parts by weight of the benzoic acid was added to an appropriate amount of aqueous ammonia to neutralize the solution, to convert partial amount (not all) of the benzoic acid to ammonium salt. The pH of the neutralized mixture was about 6 to 7 (weakly acidic). Thereafter, the mixture solution was filtered to obtain filter cake containing a mixture of the benzoic acid and the ammonium salt thereof. The chemical structure of the benzoic acid in the present embodiment was as follows:

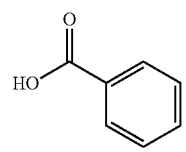

The aforementioned mixture and 5 parts by weight of colloidal silica (with a particle size of about 100 nm,) were added to 85 parts by weight of ethylene glycol, the mixture is insoluble and cannot be used as electrolyte.

Although the present invention has been described with reference to the above preferred embodiments, application of the present invention is not limited to these embodiments. It will be apparent to those skilled in the art that various modifications and variations can be made to the disclosed embodiments without departing from the scope or spirit of the disclosure. It is intended that the specification and examples be considered as exemplars only, with a true scope of the disclosure being indicated by the following claims and their equivalents.

What is claimed is:

1. A compound used in an electrolyte, having a chemical structure of:

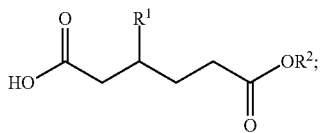

wherein $R^1$ is $C_{1-8}$ alkyl group, $C_{1-8}$ alkenyl group, $C_{1-8}$ alkynyl group, or aromatic group, $R^2$ is —$(C_nH_{2n})$—OH, and n is an integer from 2 to 8.

2. The compound used in the electrolyte as claimed in claim 1, wherein $R^1$ is a methyl group or a tert-butyl group, and n is 2.

3. An electrolyte, comprising:
an organic solvent; and
(1) a compound and an ammonium salt thereof; or a combination of (1) the compound and the ammonium salt thereof and (2) a diacid and an ammonium salt thereof, wherein the compound has a chemical structure of

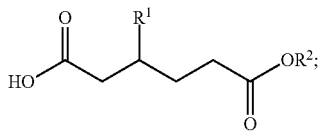

wherein $R^1$ is $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8; wherein the diacid has a chemical structure of:

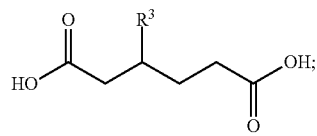

wherein $R^3$ is $C_{1-8}$ alkyl group, $C_{1-8}$ alkenyl group, $C_{1-8}$ alkynyl group, or aromatic group.

4. The electrolyte as claimed in claim 3, wherein in the combination of (1) the compound and the ammonium salt thereof and (2) the diacid and the ammonium salt thereof, (1) the compound and the ammonium salt thereof and (2) the diacid and the ammonium salt thereof have a weight ratio of 0.01:1 to 1.5.1.

5. The electrolyte as claimed in claim 3, wherein in the combination of (1) the compound and the ammonium salt thereof and (2) the diacid and the ammonium salt thereof, (1) the compound and the ammonium salt thereof and (2) the diacid and the ammonium salt thereof have a weight ratio of 0.02:1 to 0.45:1.

6. The electrolyte as claimed in claim 3, further comprising polyethylene glycol, polyvinyl alcohol, polyacryl alcohol, polyethylene oxide, propylene oxide ether, polymerized fatty acid, silicon dioxide, polyglyceride, dichromium ammonium acid, citric acid, or a combination thereof.

7. The electrolyte as claimed in claim 6, wherein the weight of (1) the compound and the ammonium salt thereof or the combination of (1) the compound and the ammonium salt thereof and (2) the diacid and the ammonium salt thereof, and the weight of polyethylene glycol, polyvinyl alcohol, polyacryl alcohol, polyethylene oxide, propylene oxide ether, polymeric fatty acid, silicon dioxide, polyglyceride, ammonium dichromate, citric acid, or a combination thereof have a ratio of 1:0.01 to 1.0.5.

8. The electrolyte as claimed in claim 3, wherein the organic solvent includes ethylene glycol, diethylene glycol, propylene glycol, 1,4-butanediol, glycerol, N,N-dimethylformamide, gamma-butyrolactone, propylene carbonate, ethylene carbonate, diethyl carbonate, diethylene glycol methyl ether, diethylene glycol monobutyl ether, gamma-valerolactone, or a combination thereof.

9. The electrolyte of claim 8, wherein the weight of (1) the compound and the ammonium salt thereof or the combination of (1) the compound and the ammonium salt thereof and (2) the diacid and the ammonium salt thereof and the weight of the organic solvent have a ratio of 16 to 1:10.

10. A capacitor, comprising:
a capacitor element, comprising:
an anode aluminum foil;
a cathode aluminum foil; and
a separator, interposed therebetween the anode aluminum foil and the cathode aluminum foil; and
an electrolyte, wherein the capacitor element is impregnated with the electrolyte,
wherein the electrolyte comprises: an organic solvent; and (1) a compound and an ammonium salt thereof or combination of (1) die compound and the ammonium salt thereof and (2) a diacid and an ammonium salt thereof, wherein the compound has a chemical structure of:

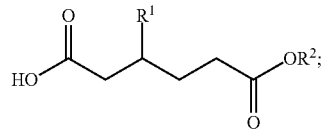

wherein $R^1$ is $C_{1-8}$ alkyl group, $C_{1-8}$ alkenyl group, $C_{1-8}$ alkynyl group, or aromatic group; and $R^2$ is —$(C_nH_{2n})$—OH, and n is an integer from 2 to 8; wherein the diacid has a chemical structure of:

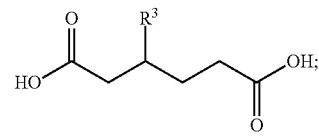

wherein $R^3$ is $C_{1-8}$ alkyl group, $C_{1-8}$ alkenyl group, $C_{1-8}$ alkynyl group, or aromatic group.

11. The capacitor as claimed in claim 10, wherein in the combination of (1) the compound and the ammonium salt thereof and (2) the diacid and the ammonium salt thereof (1) the compound and the ammonium salt thereof and (2) the diacid and the ammonium salt thereof have a weight ratio of 0.01:1 to 1.5.1.

12. The capacitor as claimed in claim 10, wherein in the combination of (1) the compound and the ammonium salt thereof and (2) the diacid and the ammonium salt thereof, (1) the compound and the ammonium salt thereof and (2) the diacid and the ammonium salt thereof have a weight ratio of 0.02:1 to 0.45:1.

13. The capacitor as claimed in claim 10, further comprising polyethylene glycol, polyvinyl alcohol, polyacryl alcohol, polyethylene oxide, propylene oxide ether, polymerized fatty acid, silicon dioxide, polyglyceride, dichromium ammonium acid, citric acid, or a combination thereof.

14. The capacitor as claimed in claim 13, wherein the weight of (1) the compound and the ammonium salt thereof or the combination of (1) the compound and the ammonium salt thereof and (2) the diacid and the ammonium salt thereof, and the weight of polyethylene glycol, polyvinyl alcohol, polyacryl alcohol, polyethylene oxide, propylene oxide ether, polymeric fatty acid, silicon dioxide, polyglyceride, ammonium dichromate, citric acid, or a combination thereof have a ratio of 1:0.01 to 1.0.5.

15. The capacitor as claimed in claim 10, wherein the organic solvent includes ethylene glycol, diethylene glycol, propylene glycol, 1,4-butanediol, glycerol, N,N-dimethylformamide, gamma-butyrolactone, propylene carbonate, ethylene carbonate, diethyl carbonate, Diethylene glycol methyl ether, diethylene glycol monobutyl ether, gamma-valerolactone, or a combination thereof.

16. The capacitor as claimed in claim 15, wherein the weight of (1) the compound and the ammonium salt thereof, or the combination of (1) the compound and the ammonium salt thereof and (2) the diacid and the ammonium salt thereof and the weight of the organic solvent have a ratio of 1:6 to 1:10.

* * * * *